United States Patent [19]

Mody et al.

[11] Patent Number: 5,210,099
[45] Date of Patent: May 11, 1993

[54] ANALGESIC COMPOSITIONS

[75] Inventors: Dhiraj S. Mody; Robert G. Blank, both of Hammonton; Gary R. Agisim, Cherry Hill; Gloria Y. Chen, Hammonton, all of N.J.

[73] Assignee: American Home Products Corporation, New York, N.Y.

[21] Appl. No.: 814,995

[22] Filed: Jan. 8, 1992

Related U.S. Application Data

[63] Continuation-in-part of Ser. No. 741,011, Aug. 6, 1991, abandoned, which is a continuation-in-part of Ser. No. 654,117, Feb. 11, 1991, abandoned.

[51] Int. Cl.⁵ ............................................... A61K 31/19
[52] U.S. Cl. ................................. 514/557; 514/871; 514/807; 514/939; 514/969
[58] Field of Search ............... 514/557, 871, 887, 939, 514/969

[56] References Cited

U.S. PATENT DOCUMENTS 4,385,049 5/1983 Cuca .
4,545,992 10/1985 Kamishita .
4,794,106 12/1988 Takashima et al. .

FOREIGN PATENT DOCUMENTS

0439344A2 7/1991 European Pat. Off. .

OTHER PUBLICATIONS

Bhala, V. H. Indian Drugs, "Transdermal Drug Delivery System for Ibuprofen", 1988, vol. 26 (3), pp. 107-111.
Gruber, K. et al. Aruzeim-Forsch/Drug Res. "Ibuprofen-Haltigen Creme", 1983, vol. 33, (II), Nr. 8, pp. 1176-1180 (with full translation).
Schaefer et al. Springer-Verlag Berlin Heidelberg N.Y. 1982, pp. 739-740.
Martin et al., Physical Pharmacy, 1983, 222-223.
Herzfeldt et al., Drug Develop. and Industrial Pharmacy vol. 9, No. 5, Aug. 1983, pp. 767-793.

*Primary Examiner*—S. J. Friedman
*Attorney, Agent, or Firm*—John W. Routh

[57] ABSTRACT

The invention provides an analgesic cream containing ibuprofen with superior skin penetration properties obtained in part by maintaining a pH of 4 to 7.2 such that the ibuprofen is suspended in substantially solid crystalline form.

8 Claims, 1 Drawing Sheet

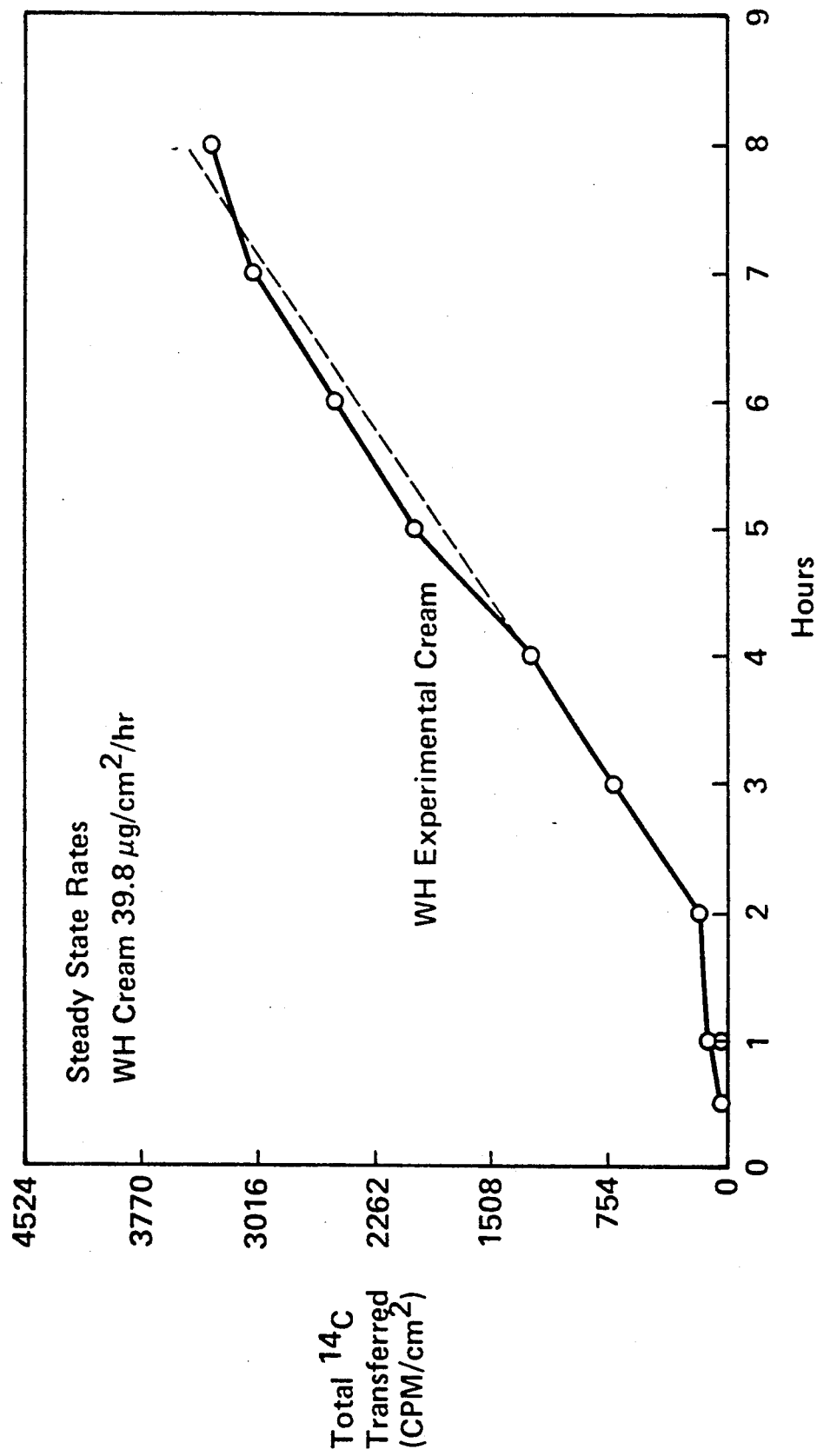
Figure 1. Transdermal Penetration of Ibuprofen ($^{14}C$) through Excised Human Skin. Steady state rates were calculated on the interval 2-8 hrs by linear regression analysis.

ANALGESIC COMPOSITIONS

This application is a continuation-in-part of Application Ser. No. 741,011, filed Aug. 6, 1991 which in turn is a continuation-in-part of Application Ser. No. 654,117, filed Feb. 11, 1991, both are abandoned.

BACKGROUND OF THE INVENTION a) Field of The Invention

This invention relates to novel topical analgesic compositions containing high concentrations of ibuprofen substantially in solid crystalline form. More particularly this invention relates to novel analgesic compositions for topical administration which are non-irritating, have superior ibuprofen skin penetration with concomitant superior analgesic effect and are cosmetically elegant. The analgesic compositions are preferably creams or lotions and comprise an oil-in-water emulsion having a pH at which the ibuprofen is maintained in substantially solid form suspended in the emulsion.

b) Description of Related Art

There is described in U.S. Pat. No. 4,385,049 a topical preparation system, for example, for pharmaceutical products such as non-steroidal antiinflammatory agents, which are water-in-oil emulsions containing particular emulsifiers. No examples of non-steroidal antiinflammatory drugs are given. An oil-in-water type emulsion is described in U.S. Pat. No. 4,794,106 which is a cream containing hydrocortisone butyrate propionate as the active ingredient and having a pH preferably of 4.5 to 5.5 to increase the storage stability of the hydrocortisone butyrate propionate.

SUMMARY OF THE INVENTION

According to this invention a cosmetically elegant analgesic composition is provided for topical administration containing high concentrations of ibuprofen substantially in solid crystalline form dispersed or suspended in an oil-in-water emulsion. The analgesic compositions are preferably lotions or creams, have an ibuprofen content of about 5% up to about 12% by weight, are non-irritating to the skin, and have superior skin penetration with concomitant enhanced analgesic effect. The analgesic compositions have a pH of about 4 to about 7.2, preferably 5 to 5.8, such that the ibuprofen is substantially in solid crystalline form, i.e., at least about 70% by weight in solid crystalline form, and preferably about 95% to 100% by weight in solid crystalline form, and the ibuprofen which is dissolved is partially in neutral or non-charged form. The compositions are oil-in water emulsions containing about 60% to about 90% by weight of water, preferably about 70% to about 80% by weight of water, and the oil phase of the emulsion is composed of emollient constituents that do not dissolve the ibuprofen to any great extent at a pH of 4-7. In order to minimize dissolution of the ibuprofen, advantageously the ibuprofen is added after the oil phase and the aqueous phase are emulsified to form the oil-in-water emulsion and when the temperature of the oil-in-water emulsion is below the melting point of ibuprofen, i.e. about 74°-80° C., and preferably the temperature is below about 35° C.

Not wishing to be bound by any theory of the invention but partially in explanation thereof, the following is presented.

An article by C.D. Herzfeldt and R. Kummel in "Drug Development and Industrial Pharmacy", Volume 9, No. 5, Aug. 1983 at page 784 sets forth the dissociation constant (pka) for ibuprofen in water as 5.3. In accordance with the well known Henderson-Hasselbalch Equation (described in Physical Pharmacy, Third Edition, Alfred Martin et al, Lea & Febiger, 1983 at page 223), at a pH of 5.3 half of the dissolved ibuprofen will be in the ionized form and half in the nonionized form. Similarly, at a pH equal to the pka plus one, i.e. 6.3, according to the Henderson-Hasselbalch Equation, 90% of the dissolved ibuprofen would be in the ionized form and 10% in the nonionized form. The Herzfeldt and Kummel article also on page 784 graphs the solubility of ibuprofen in water at various pH levels and indicates that ibuprofen is soluble to a very limited degree at a pH of 6. Hence the compositions of the invention are formulated so as to provide substantially all of the ibuprofen in solid crystalline form as a reservoir by (1) limiting the ibuprofen in ionized form by maintaining the pH between about 4 and about 7.2 so as not to solubilize the ibuprofen in the aqueous phase, (2) selecting the components of the oil phase so as not to dissolve the ibuprofen to any great extent at a pH of 4–7, and (3) incorporating an excess of ibuprofen in the formulation, ie about 5–12% by weight.

DETAILS OF THE INVENTION

Ibuprofen useful in forming the analgesic compositions of the invention can be obtained commercially in crystalline powder form. By powder form is meant finely divided having an average particle size of about 20 microns to about 50 microns. Commercial grades are available having an average particle size of 40 microns.

The oil phase of the emulsion can be composed of the usual emollient constituents so long as they do not dissolve the ibuprofen to any great extent at a pH of 4–7. Suitable emollient constituents are lanolin and lanolin alcohol fractions, cetyl alcohol, stearyl alcohol, lactate glyceryl stearates, glyceryl oleates, mineral oil, petrolatum, paraffin, beeswax, hexadecyl dimethicone, and the like. Note, for example, U.S. Pat. No. 3,154,470 to Ernest Braun incorporated herein by reference in its entirety.

Suitable emulsifiers include the known non-ionic polyalkyleneoxy ether alcohol type oil-in-water emulsifiers such as oxyalkylated glycols, glycerol, hexitols and fatty alcohols, glyceryl stearate, and the like.

Various optional ingredients may be included in the formulation. Such optional ingredients include perfumes; preservatives, e.g. parabens; antiseptics, e.g. zinc oxide micronized; pigments; humectants, e.g. glycerin; antioxidants; chelating agents, e.g. disodium EDTA; stabilizers, e.g. xanthan gum, carboxy-vinyl polymers, carboxymethyl cellulosics; dyes; antifoam agents; viscosity control agents, e.g. smectic minerals; trolamine; healing agents, e.g. skin respiratory factor, as well as any other class or material whose presence may be cosmetically or otherwise desirable.

The preparation of the formulations in accordance with the invention is illustrated in the following examples.

EXAMPLE 1

The following ingredients were incorporated into the analgesic cream of the invention.

| Ingredient | Weight % |
|---|---|
| Part I - Oil Phase | |
| Glyceryl Stearate, NF | 2.00 |
| Lexate TA* | 3.00 |
| Mineral Oil, USP | 3.00 |
| Acetylated Lanolin, NF | 2.00 |
| Cetyl Alcohol, NF | 2.00 |
| Laureth - 23** | 0.75 |
| Propylparaben, NF | 0.10 |
| Part II - Water Phase | |
| Purified Water Deionized, USP | 72.42 |
| Glycerin 96%, USP | 2.00 |
| Methylparaben, NF | 0.20 |
| Imidurea, NF | 0.30 |
| Carbopol - 940*** | 0.40 |
| Part III | |
| Purified Water Deionized, USP | 0.75 |
| Part IV | |
| Purified Water Deionized, USP | 1.00 |
| Sodium Hydroxide, NF | 0.08 |
| Part V | |
| Ibuprofen, USP | 10.00 |
| | 100.00% |

*Lexate TA is a mixture of glyceryl stearate, isopropyl myristate and stearyl stearate.
**Laureth-23 is a lauryl alcohol ether of PEG
***Carbobol - 940 is a crosslinked polymer of acrylic acid The cream of this example was prepared by methods well known in the art for preparing oil-in-water emulsions. The oil-phase (Part I) is heated in a kettle equipped with a mixer to 75°–80° C. with mixing. The water phase (Part II) is placed into a separate larger vessel equipped with a mixer and the solids dissolved therein while heating to 70°–75° C. Transfer oil phase into water phase with mixing, rinsing the kettle with water (Part III) and transferring the rinsings to the water phase. Cool the emulsion to 35° C. and add the sodium hydroxide solution (Part IV) with mixing and cooling to 30° C. Homogenize until the cream is smooth and uniform. Gradually add the ibuprofen powder (Part V) with mixing while maintaining the temperature at 25°–30° C. Turn off the homogenizer and continue mixing for 1 to 2 hours, then transfer the cream into a double poly-lined drum.

The product was an odorless smooth, white soft cream having pH (salt bridge) of 5.36, a specific gravity at 25° C. of 1.0429 and a viscosity (TB/4RPM) 25° C. of 58,900 cps.

EXAMPLE 2

The following ingredients were incorporated into the analgesic cream of this invention.

| Ingredient | Weight % | Grams |
|---|---|---|
| Part I - Oil Phase | | |
| Mineral Oil, USP | 3.00 | 120 |
| Isopropyl Myristate, NF | 4.00 | 160 |
| Stearic Acid, NF | 0.75 | 30 |
| Cerasynt 945* | 1.50 | 60 |
| Propylparaben, NF | 0.05 | 2 |
| Part II - Water Phase | | |
| Purified Water Deionized, USP | 75.58 | 3,100 |
| Glycerin 99%, USP | 2.00 | 80 |
| Methylparaben, NF | 0.20 | 8 |
| Imidurea, NF | 0.15 | 6 |
| Disodium Edetate, USP | 0.05 | 2 |
| Carbopol 940 | 0.85 | 34 |
| Part III | | |
| Ibuprofen, USP | 10.00 | 400 |
| Part IV | | |
| Purified Water Deionized, USP | 1.70 | 68 |
| Sodium Hydroxide, NF | 0.17 | 6.8 |
| | 100.00 | |

*Cerasynt 945 contains glyceryl stearate and the lauryl alcohol ether of PEG

The cream of this example was prepared similarly as in Example 1. The oil phase (Part I) was placed in a glass beaker fitted with a Lighting Mixer and heated to 75°–80° C. with continuous mixing until a uniform liquid was formed. The water phase (Part II) was formed in a jacketed stainless steel mixing vessel fitted with a Homo Mixer. First the water was added to the vessel, part being withheld for rinsing, and then the other liquids were added and mixed until all dissolved, the methylparaben was then added and suspended and the Carbopol 940- was sprinkled on the surface until completely dispersed. The Homo Mixer (vertex assembly) was used until the Carbopol 940 was fully hydrated and the product was lump-free. The water phase was then heated to 70°–75° C. while mixing continuously. The oil phase was then transferred to the water phase and the glass beaker was rinsed with the withheld water, the rinsing being added. The mixing was continued to form the emulsion and the product was cooled to 35° C. The ibuprofen (Part III) was gradually added while cooling and mixing continued until the ibuprofen was uniformly distributed. The sodium hydroxide dissolved in another portion of water (Part IV) was then added to the emulsion while mixing and the product was cooled to 25°–30° C., deaerated, and transferred to a storage container. The product was an odorless smooth white soft cream having a pH of 5.45 (salt bridge), a specific gravity of 1.010 at 25° C. and a viscosity (TB/4RPM) 25° C. of 53,000 cps.

EXAMPLE 3

The following ingredients were incorporated into the analgesic cream of this invention.

| Ingredient | Weight % |
|---|---|
| Part I - Oil Phase | |
| Mineral Oil, USP | 3.00 |
| Stearic Acid, NF | 0.75 |
| Cerasynt 945 | 1.50 |
| Hexadecyl Dimethicone | 2.00 |
| Propylparaben, NF | 0.05 |
| Part II - Water Phase | |
| Purified Water Deionized, USP | 79.28 |
| Glycerin 99%, USP | 2.00 |
| Methylparaben, NF | 0.20 |
| Imidurea | 0.15 |
| Disodium Edetate, USP | 0.05 |
| Carbopol 940 | 0.85 |
| Part III | |
| Ibuprofen, USP | 10.00 |
| Part IV | |
| Sodium Hydroxide, NF | 0.17 |
| | 100.00 |

The ingredients were mixed similarly as in Example 2 and the product again was an odorless, smooth, soft white cream having a pH of 5.56 (salt bridge) a specific gravity of 1.011 at 25° C. and a viscosity (TB/4RPM) 25° C. of 50,000 cps.

EXAMPLE 4

In this example, the object of the experimental work was to determine the level of sodium ibuprofen in the analgesic cream of Example 2 and to determine the effect of pH levels of about pH 7 on the skin penetration properties of the analgesic cream.

A stock cream in the amount of about six kilograms (5580 grams) was prepared with the same proportions of and the same ingredients as in Example 2 except that the ibuprofen was omitted. This stock cream was divided into two aliquots hereinafter designated Stock 1 and Stock 2.

Stock 1 served as a placebo, while Stock 2 represented an analgesic cream of the invention containing 5.1% by weight of ibuprofen formed by adding 150 grams of ibuprofen to 2790 grams of the second aliquot while mixing in a Hobart Bowl fitted with a Lightning Mixer for thirty minutes at room temperature.

Stock 1 and Stock 2 were then titrated with a 10% by weight sodium hydroxide solution as shown in the following titration summary. The amounts of sodium hydroxide are given in weight percent pure sodium hydroxide based on the weight of the total composition which for each of Stock 1 and Stock 2 was 930 grams and 980 grams respectively. After each addition of sodium hydroxide solution, the composition was mixed in a Hobart Mixer with blade for ten minutes.

TITRATION SUMMARY

| NaOH % w/w | Stock 1 (Placebo) pH | Stock 1 (Placebo) Viscosity, CPS | Stock 2 (Active) ph | Stock 2 (Active) Viscosity, CPS |
| --- | --- | --- | --- | --- |
| 0 | 3.04 | 12,750 | 3.10 | 8,000 |
| 0.055 | 4.24 | | | |
| 0.109 | 4.86 | | 4.89 | |
| 0.142 | 5.15 | 81,000 | 5.16 | 80,000 |
| 0.219 | 5.73 | | | |
| 0.328 | 6.45 | | 6.39 | |
| 0.352 | 6.67 | | | |
| 0.384 | 6.86 | | | |
| 0.416 | 7.13 | 69,400 | | |
| 0.437 | 7.34 | | | |
| 0.459 | 7.57 | 66,000 | 6.62 | |
| 0.547 | | | 6.85 | |
| 0.601 | | | 6.93 | |
| 0.656 | | | 7.01 | |
| 0.711 | | | 7.13 | 31,200 |

On the fourth line of the Summary, at 0.142% by weight sodium hydroxide, Stock 1 has a pH of 5.15 and a viscosity of 81,000 cps, almost identical to the values for Stock 2. This indicates that all of the sodium hydroxide is neutralized by the pre-hydrated Carbopol 940. The comparable viscosities also support this position. Accordingly these data indicate that all of the ibuprofen is in the nonionized crystalline state.

On the sixth line of the Summary, at 0.328% by weight sodium hydroxide, again Stock 1 and Stock 2 have a similar pH similarly indicating that the ibuprofen remains totally in the nonionized form. It is significant to note that in the previous three examples, the sodium hydroxide content is 20% of that of the Carbopol 940. At this ratio of sodium hydroxide to Carbopol 940, the pH should remain between 5–5.8 and the ibuprofen should essentially be completely in the nonionized form.

On the ninth line of the Summary, at 0.416% by weight sodium hydroxide, Stock 1 has a pH of 7.13 and a viscosity of 69,400 while Stock 2 does not reach a pH of 7.13 (the last line of the Summary) until 0.711% by weight sodium hydroxide has been added at which point the viscosity has decreased to 31,200. This indicates that the excess sodium hydroxide i.e. 2.943 grams has reacted with the ibuprofen to form the sodium salt. Calculations show that on a percent weight by weight basis, of the 5% by weight ibuprofen in Stock 2, at a pH of 7.13, 1.5% by weight of the ibuprofen is in the ionized form and 3.5% by weight of the ibuprofen is in the nonionized form. Accordingly of the total ibuprofen content of Stock 2, at a pH 7.13, 30% by weight is in the ionized form and 70% by weight is in the nonionized form. The viscosity of Stock 1 at a pH of 7.13 of 69,400 cps as compared to the viscosity of Stock 2 at a pH of 7.13 of 31,200 cps represents a "salting out" of the salt-sensitive Carbopol 940 by the sodium ibuprofen.

Carbopol 940 is one of a series of synthetic, high molecular weight, non-linear polymers of acrylic acid cross-linked with a polyalkenyl polyether containing between 98.7% and 99.9% acrylic acid. Molecular weights of Carbomers - 934, - 940, and -941 range from approximately 500,000 to 4,000,000. The carbomers are finely divided, free-flowing powders which are hygroscopic in nature and swell to many times their original volume, although "maximum volume swell" does not occur in water until the polymers are converted to partial organic or inorganic salts. Maximum volume occurs at 50–90% neutralization with a neutralization of 75% normally occurring at pH 7.

The analgesic creams of this invention have good application characteristics and low irritancy potential. The cream of Example 1 exhibits some "whitening" on application which disappears with continued rub-in. The cream of Examples 2 and 3 absorb readily into the skin leaving no white residue or any white particles. Microscopic analysis of the analgesic creams of examples 1–4 shows crystalline materials in all samples.

EXAMPLE 5

The traditional way of assessing topical drug delivery in vitro has been to do diffusion cell experiments which measure transdermal penetration, it being assumed that the rate of appearance of the drug in the receptor chamber will be proportional to the rate of transfer of drug to the dermal capillary network in vivo.

In this experiment, excised full-thickness human skin was used; thus the appendages as well as the keratinized surface layers are intact. A use-level dose of the formulation (5–10 mg/cm$^2$) is applied to the surface, and in a typical case, only a small percentage of the dose diffuses through the skin during the course of the experiment. For this reason, steady state conditions can prevail after a lag period, and a rate, in mass transferred/cm$^2$/hr determined.

Five samples were assessed for transdermal penetration of ibuprofen in two test procedures, the first using excised human abdominal skin and the second using excised human skin obtained from a breast reduction. In each procedure, one gram of test vehicle was mixed with 5 $\mu$ Ci of Carbon 14 ibuprofen and held at 32° C. for three days prior to the test.

BRIEF DESCRIPTION OF DRAWING

FIG. 1 of the drawings is a graph showing the transdermal penetration of the Carbon 14 tagged ibuprofen (sample of Example 2) through excised human skin in such a diffusion experiment wherein radiation Counts Per Minute per square centimeter is plotted against time in Hours with the steady state rate being calculated on the interval 2-8 hours by linear regressive analysis.

In the first test, a sample of Example 2 containing 10% by weight of ibuprofen was compared with a sample of DOLGIT, a commercial product containing 5% by weight of ibuprofen marketed by Dolorgiet Pharmaceuticals, Germany. The steady state rate for the sample of Example 2 was 38.8 micrograms/c$^2$/hour while the steady state rate for DOLGIT was 4.5 micrograms/cm$^2$/hour.

In the second test, a sample of DOLGIT was compared with two samples of Stock 2 of Example 4, the first sample having a pH of 5.16 and the second sample having a pH of 7.13. All three samples in the second test contained 5% by weight of ibuprofen and the steady state rates were as follows in micrograms/cm$^2$/hour:

| DOLGIT | STOCK 2 (pH 5.16) | STOCK 2 (pH 7.13) |
|---|---|---|
| 1.15 | 2.22 | 3.61 |

Although the observed differences among the three products were statistically significant, this was not a definitive study since the comparison was done on a single skin sample, as evidenced by the steady state rate for DOLGIT in the first test on a different skin sample.

The steady state rate for the cream of Example 2 is shown in FIG. 1 attached and was 39.8 μg/cm$^2$/hr.

Penetration enhancers can be employed with the analgesic compositions of this invention, i.e. menthol as described in U.S. Pat. No. 4,931,283 to Andrew G. Tsuk.

As a general rule, in the manufacturing procedure and/or selection of emollient constituents, emulsifiers and the like, techniques and selections should be made to minimize ibuprofen solubility. Thus alcohols or glycols such as propylene glycol should be avoided in both the water and oil phases. In another instance, if an acidic polymeric material such as Carbopol 940 is employed, it should be pre-hydrated in the aqueous phase before the addition of an alkali, such as sodium hydroxide, so that the alkali preferentially neutralizes the acidic polymeric material.

We claim:

1. A topical anagesic composition consisting essentially of an oil-in-water emulsion containing about 5% to about 12% by weight of ibuprofen, the emulsion containing about 60% to about 90% by weight of water and having minimum ibuprofen solubility characteristics in both the water and oil phases, the composition having a pH of about 4 to about 7.2 such that at least about 70% by weight of the ibuprofen is suspended in the emulsion in substantially solid crystalline form.

2. The topical analgesic composition of claim 1 wherein the pH of the composition is 5 to 5.8 and about 95% to about 100% by weight of the ibuprofen is suspended in solid crystalline form.

3. The topical analgesic composition of claim 1 wherein the composition contains about 70% to about 80% water by weight.

4. The topical analgesic composition of claim 1 wherein the ibuprofen is added to the oil-in-water emulsion at a temperature below the melting point of ibuprofen.

5. The topical analgesic composition of claim 1 wherein the oil phase of the emulsion consists essentially of emollient constituents that do not dissolve the ibuprofen to any great extent at pH of 4-7 selected from the class consisting of lanolin, lanolin alcohol fractions, cetyl alcohol, stearyl alcohol, stearic acid, lactates, glycerin, glyceryl stearates, glyceryl oleates, stearyl stearates, isopropyl myristate, mineral oil, pertrolatum, paraffin, beeswax and hexadecyl dimethicone, wherein the pH of the composition is 5 to 5.8, wherein about 95% to about 100% by weight of ibuprofen is suspended in solid crystalline form wherein the composition contains about 70% to about 80% water by weight and wherein the ibuprofen in solid crystalline form is added to the oil-in-water emulsion at a temperature below about 35° C.

6. The topical analgesic composition of claim 5 additionally containing an alkali and about 0.4 to about 0.85% by weight of the total composition of a polymer of acrylic acid cross-linked with a polyalkenyl polyether, the polymer having a molecular weight between 500,000 and 4,000,000, and the amount of alkali being not greater than 20% buy weight of the polymer.

7. A topical analgesic composition consisting essentially of an oil-in-water emulsion containing about 5% to about 12% by weight of ibuprofen, the emulsion containing about 70% to a 80% by weight of water and having minimum ibuprofen solubility characteristics in both the oil and water phases, the composition having a pH of 5 to 5.8 such that about 95% to about 100% by weight of the ibuprofen is suspended in the emulsion in solid crystalline form, the ibuprofen being added to the oil-in water emulsion in solid crystalline form at a temperature below about 35° C., and the topical analgesic composition additionally containing an alkali and about 0.4 to about 0.85% by weight of the total composition of a polymer of acrylic acid cross-linked with a polyalkenyl polyether, the polymer having a molecular weight between 500,000 and 4,000,000, and the amount of alkali being not greater than 20% by weight of the polymer.

8. The topical analgesic composition of claim 7 wherein the oil phase of the emulsion consists essentially of emollient constituents that do not dissolve the ibuprofen to any great extent at a pH of 4-7 selected from the class consisting of lanolin, lanolin alcohol fractions, cetyl alcohol, stearyl alcohol, stearic acid, lactates, glycerin, glyceryl stearates, glyceryl oleates, stearyl stearates, isopropyl myristate, mineral oil, petrolatum, paraffin, beeswax and hexadecyl dimethicone.

* * * * *